United States Patent
Rioux et al.

(10) Patent No.: US 11,849,926 B2
(45) Date of Patent: Dec. 26, 2023

(54) BONE MARROW ACCESS APPARATUS

(71) Applicant: APERTURE MEDICAL TECHNOLOGY LLC, New York, NY (US)

(72) Inventors: Bob Rioux, Ashland, MA (US); Khoder Jaber, Sharon, MA (US)

(73) Assignee: APERTURE MEDICAL TECHNOLOGY LLC, New York, NY (US)

(*) Notice: Subject to any disclaimer, the term of this patent is extended or adjusted under 35 U.S.C. 154(b) by 223 days.

(21) Appl. No.: 16/559,870

(22) Filed: Sep. 4, 2019

(65) Prior Publication Data
US 2019/0388067 A1 Dec. 26, 2019

Related U.S. Application Data

(63) Continuation of application No. 15/486,870, filed on Apr. 13, 2017, now Pat. No. 10,517,576.
(Continued)

(51) Int. Cl.
*A61B 10/02* (2006.01)
*A61B 17/86* (2006.01)
(Continued)

(52) U.S. Cl.
CPC .......... *A61B 10/025* (2013.01); *A61B 17/164* (2013.01); *A61B 17/1615* (2013.01);
(Continued)

(58) Field of Classification Search
CPC .......... A61B 10/025; A61B 2010/0258; A61B 17/1637; A61B 17/164; A61B 17/1635;
(Continued)

(56) References Cited

U.S. PATENT DOCUMENTS 2,219,605 A 10/1940 Henry
2,919,692 A 1/1960 Wolfgang
(Continued)

FOREIGN PATENT DOCUMENTS

CN 104414714 A 3/2015
GB 1324759 A 7/1973
(Continued)

OTHER PUBLICATIONS

Islam, "Induction treatment of acute myeloid leukemia in an elderly patient with intramarrow injection/administration of cytarabine: first report of a case", Clinical Case Reports 2015; 3(12): 1026-1029.
(Continued)

*Primary Examiner* — Matthew J Lawson
(74) *Attorney, Agent, or Firm* — Holtz, Holtz & Volek PC

(57) ABSTRACT

A bone marrow access apparatus includes a bone penetrating member having an internal channel having an opening at a proximal end and an opening at a distal end. A valve cap is engaged with the bone penetrating member, the valve cap defining an interior cavity in which part of the bone penetrating member is situated. The valve cap includes a valve having an opening having an open state in which the channel is not obstructed and a closed state to prevent flow of a material through the channel. The valve is repeatedly switchable between the open and closed states. The bone penetrating member has an upper surface and a seat which is below the upper surface, the seat being located at an interior of the bone penetrating member, and the seat being engageable with an installation or removal instrument.

5 Claims, 6 Drawing Sheets

Related U.S. Application Data

(60) Provisional application No. 62/404,551, filed on Oct. 5, 2016.

(51) Int. Cl.
*A61B 17/34* (2006.01)
*A61B 17/16* (2006.01)
*A61B 17/68* (2006.01)
*A61B 17/00* (2006.01)

(52) U.S. Cl.
CPC .......... *A61B 17/34* (2013.01); *A61B 17/3417* (2013.01); *A61B 17/3423* (2013.01); *A61B 17/3472* (2013.01); *A61B 17/3498* (2013.01); *A61B 17/864* (2013.01); *A61B 17/3462* (2013.01); *A61B 17/685* (2013.01); *A61B 17/8635* (2013.01); *A61B 2010/0258* (2013.01); *A61B 2017/00685* (2013.01); *A61B 2017/3419* (2013.01)

(58) Field of Classification Search
CPC ............ A61B 17/3417; A61B 17/3423; A61B 17/3472; A61B 17/3498
See application file for complete search history.

(56) References Cited

U.S. PATENT DOCUMENTS

| | | |
|---|---|---|
| 4,142,517 A | 3/1979 | Contreras et al. |
| 4,403,617 A | 9/1983 | Tretinyak |
| 4,519,514 A | 5/1985 | Agbay et al. |
| 4,738,261 A | 4/1988 | Enstrom |
| 4,772,261 A * | 9/1988 | Von Hoff ............... A61B 17/68 604/175 |
| 5,104,389 A | 4/1992 | Deem et al. |
| 5,122,114 A | 6/1992 | Miller et al. |
| 5,273,545 A | 12/1993 | Hunt et al. |
| 5,332,398 A | 7/1994 | Miller et al. |
| 5,372,583 A * | 12/1994 | Roberts ................. A61M 25/06 604/506 |
| 5,405,388 A | 4/1995 | Fox |
| 5,451,210 A | 9/1995 | Kramer et al. |
| 5,456,267 A | 10/1995 | Stark |
| 5,601,559 A | 2/1997 | Melker et al. |
| 5,720,753 A | 2/1998 | Sander et al. |
| 5,727,770 A * | 3/1998 | Dennis ............... A61B 17/3462 251/149.1 |
| 5,743,861 A | 4/1998 | Columbus et al. |
| 5,817,062 A | 10/1998 | Flom et al. |
| 5,990,382 A | 11/1999 | Fox |
| 6,018,094 A | 1/2000 | Fox |
| 6,033,369 A | 3/2000 | Goldenberg |
| 6,165,168 A | 12/2000 | Russo |
| 7,670,328 B2 | 3/2010 | Miller |
| 7,833,204 B2 | 11/2010 | Picha |
| 7,951,089 B2 | 5/2011 | Miller |
| 8,079,979 B2 | 12/2011 | Moorehead |
| 8,142,365 B2 | 3/2012 | Miller |
| 8,372,061 B2 | 2/2013 | Berna et al. |
| 8,419,683 B2 | 4/2013 | Miller et al. |
| 8,500,819 B2 | 8/2013 | Meridew et al. |
| 8,690,791 B2 | 4/2014 | Miller |
| 8,715,287 B2 | 5/2014 | Miller |
| 8,801,670 B2 | 8/2014 | Drontle et al. |
| 8,852,119 B2 | 10/2014 | Wawrzyniak et al. |
| 8,870,872 B2 | 10/2014 | Miller |
| 8,876,826 B2 | 11/2014 | Miller |
| 8,992,442 B2 | 3/2015 | Cortes Ramirez et al. |
| 8,992,535 B2 | 3/2015 | Miller |
| 8,998,848 B2 | 4/2015 | Miller et al. |
| 9,072,543 B2 | 7/2015 | Miller et al. |
| 9,078,637 B2 | 7/2015 | Miller |
| 9,125,639 B2 | 9/2015 | Mathis et al. |
| 9,301,736 B2 | 4/2016 | Rusnak |
| 9,314,228 B2 | 4/2016 | Miller |
| 9,433,400 B2 | 9/2016 | Miller |
| 9,451,968 B2 | 9/2016 | Miller et al. |
| 9,770,425 B2 | 9/2017 | Solomon |
| 10,426,940 B2 | 10/2019 | Aklog et al. |
| 10,448,933 B2 | 10/2019 | Rioux et al. |
| 2002/0082519 A1 | 6/2002 | Miller et al. |
| 2003/0032922 A1 | 2/2003 | Moorehead |
| 2003/0093034 A1 | 5/2003 | Chang et al. |
| 2003/0225344 A1 | 12/2003 | Miller |
| 2004/0127905 A1 | 7/2004 | Lim et al. |
| 2004/0215102 A1 | 10/2004 | Ikehara et al. |
| 2005/0148940 A1 | 7/2005 | Miller |
| 2005/0209607 A1 * | 9/2005 | Lipchitz ............. A61B 17/3498 606/108 |
| 2006/0167378 A1 | 7/2006 | Miller |
| 2006/0167379 A1 | 7/2006 | Miller |
| 2006/0167416 A1 | 7/2006 | Mathis et al. |
| 2006/0247552 A1 | 11/2006 | Ikehara et al. |
| 2007/0088277 A1 | 4/2007 | Mcginley et al. |
| 2007/0197935 A1 | 8/2007 | Reiley et al. |
| 2007/0270712 A1 | 11/2007 | Wiksell et al. |
| 2007/0270775 A1 | 11/2007 | Miller et al. |
| 2008/0015467 A1 | 1/2008 | Miller |
| 2008/0015468 A1 | 1/2008 | Miller |
| 2008/0065083 A1 | 3/2008 | Truckai et al. |
| 2008/0215056 A1 | 9/2008 | Miller et al. |
| 2008/0287910 A1 | 11/2008 | Picha |
| 2009/0054808 A1 | 2/2009 | Miller |
| 2010/0137740 A1 | 6/2010 | Miller |
| 2010/0234761 A1 | 9/2010 | Cortes et al. |
| 2010/0298784 A1 | 11/2010 | Miller |
| 2011/0076640 A1 * | 3/2011 | Jones ...................... A61C 8/00 433/80 |
| 2011/0137352 A1 | 6/2011 | Biedermann et al. |
| 2011/0218644 A1 | 9/2011 | Meridew et al. |
| 2012/0095440 A1 | 4/2012 | Islam |
| 2012/0116247 A1 | 5/2012 | Wawrzyniak et al. |
| 2013/0190817 A1 | 7/2013 | Bouduban et al. |
| 2013/0304116 A1 | 11/2013 | Yamane |
| 2014/0018699 A1 | 1/2014 | Rusnak |
| 2014/0150782 A1 | 6/2014 | Vazales et al. |
| 2014/0206941 A1 * | 7/2014 | Stiner ................. A61B 17/3417 29/428 |
| 2014/0207084 A1 * | 7/2014 | Webb .................. A61B 17/3462 604/264 |
| 2014/0288499 A1 | 9/2014 | Miller |
| 2015/0314118 A1 | 11/2015 | Kelekis et al. |
| 2016/0015893 A1 | 1/2016 | Hoyt et al. |
| 2016/0136410 A1 | 5/2016 | Aklog et al. |
| 2016/0331401 A1 * | 11/2016 | Dreyfuss ............ A61B 17/3421 |
| 2017/0216564 A1 | 8/2017 | Devgon et al. |
| 2018/0092662 A1 | 4/2018 | Rioux et al. |
| 2018/0093094 A1 | 4/2018 | Wolf |
| 2018/0256869 A1 | 9/2018 | Aklog et al. |
| 2019/0388066 A1 | 12/2019 | Rioux et al. |
| 2020/0113552 A1 | 4/2020 | Rioux |
| 2023/0191100 A1 * | 6/2023 | Miller .................. A61M 39/26 604/180 |

FOREIGN PATENT DOCUMENTS

| | | |
|---|---|---|
| GB | 2289415 A | 11/1995 |
| JP | S535654 U | 1/1978 |
| JP | H03111025 A | 5/1991 |
| JP | 2001104323 A | 4/2001 |
| JP | 2003116862 A | 4/2003 |
| JP | 2013233283 A | 11/2013 |
| WO | 2014070804 A1 | 5/2014 |
| WO | 2016057090 A1 | 4/2016 |
| WO | 2020076543 A1 | 4/2020 |

OTHER PUBLICATIONS

Rosetti, et al., "Intraosseous Infusion: An Alternative Route of Pediatric Intravascular Access", Annals of Emergency Medicine, 14:Sep. 9, 1985, pp. 885-888.

(56) References Cited

OTHER PUBLICATIONS

Related U.S. Appl. No. 16/158,568, First Named Inventor: Bob Rioux, Title: "Bone Marrow Access Apparatus and Methods for Locating Same", filed Oct. 12, 2018.
Extended European Search Report (EESR) dated Apr. 23, 2020 issued in European Patent Application No. 17858996.6.
International Search Report (ISR) and Written Opinion dated Sep. 30, 2015 issued in International Application No. PCT/US2015/036407.
International Search Report for PCT/US2017/054883 dated Jan. 18, 2018.
Notice of Allowance dated Jun. 6, 2019 issued in U.S. Appl. No. 15/486,886.
Written Opinion for PCT/US2017/054883 dated Jan. 18, 2018.
Japanese Office Action (and English language translation thereof) dated Jul. 22, 2020 issued in Japanese Application No. 2019-518968.
Notice of Allowance dated Jul. 27, 2021 issued in related U.S. Appl. No. 16/559,811.
Extended European Search Report (EESR) dated Jun. 2, 2021 issued in European Application No. 21157097.3.
International Search Report (ISR) and Written Opinion dated Feb. 5, 2020 issued in International Application No. PCT/US2019/053920.
Japanese Office Action (and English language translation thereof) dated Jan. 19, 2022, issued in counterpart Japanese Application No. 2021-025913.
Partial Supplementary European Search Report dated Jan. 31, 2022, issued in European Application No. 19871573.2.
Japanese Office Action (and English language translation thereof) dated Jun. 15, 2022, issued in Japanese Application No. 2021-519727.
Japanese Office Action (and English language translation thereof) dated Sep. 7, 2022, issued in counterpart Japanese Application No. 2021-025913.
Notice of Allowance dated May 20, 2022, issued in related U.S. Appl. No. 16/158,568.
Japanese Office Action (and English language translation thereof) dated Jan. 4, 2023, issued in Japanese Application No. 2021-519727.

* cited by examiner

FIG. 16
FIG. 9
FIG. 12
FIG. 14
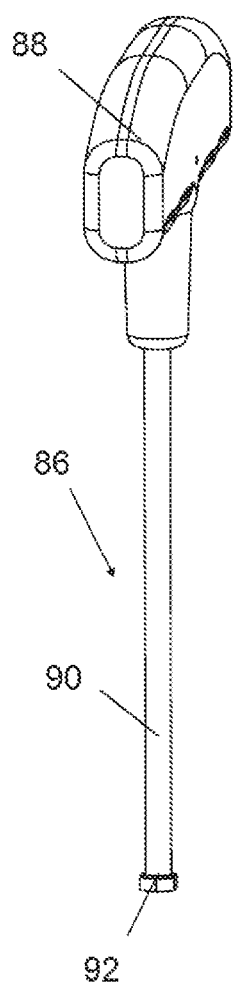
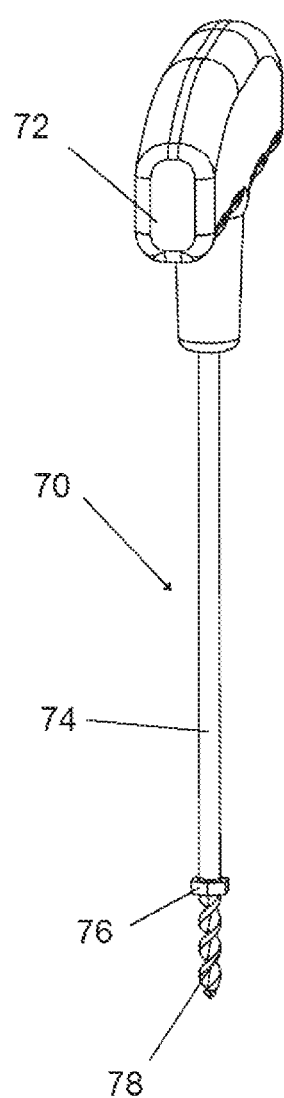
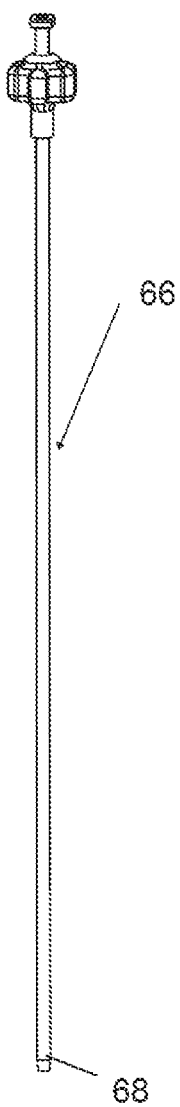
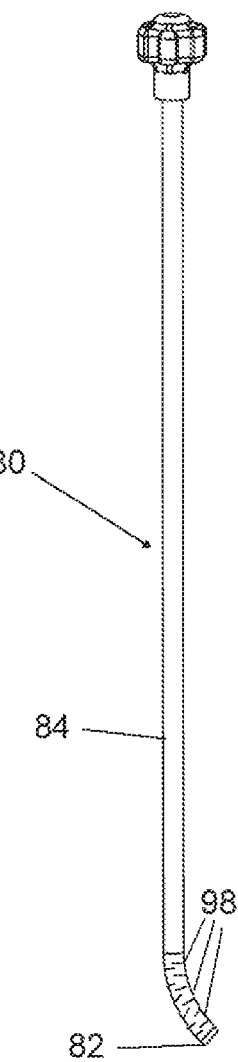

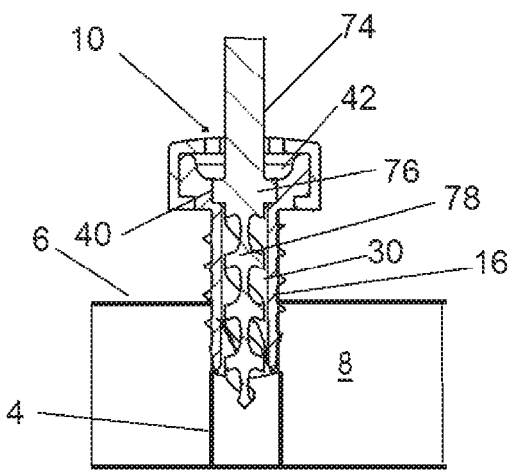
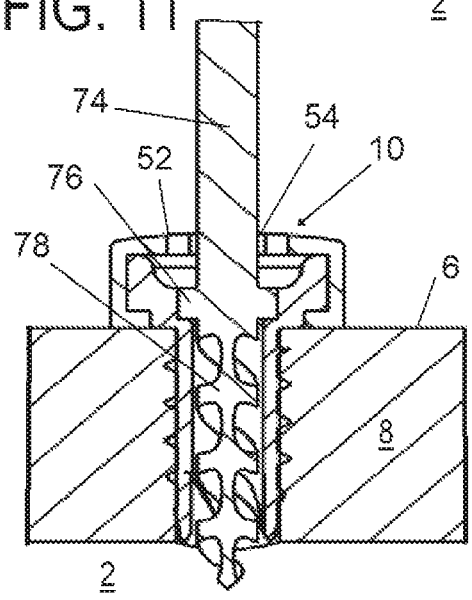
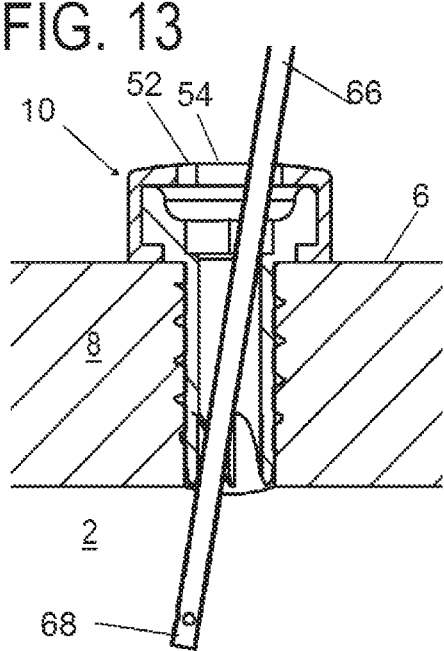

BONE MARROW ACCESS APPARATUS

CROSS REFERENCE TO RELATED APPLICATION

This application is Continuation of U.S. patent application Ser. No. 15/486,870, filed Apr. 13, 2017, the entire contents of which are incorporated herein by reference.

FIELD OF THE INVENTION

The present invention relates generally to a bone marrow access system including a bone marrow access apparatus capable of providing easy, repeatable access to a patient's bone marrow, tools for installing and removing the bone marrow access apparatus, and instruments for use with the bone marrow access apparatus when installed.

BACKGROUND OF THE INVENTION

Bone marrow is the major site of blood cell formation and, while at birth it is found within nearly all bones, by adolescence it is located primarily within axial bones (e.g., pelvis and femur). The bone marrow exists in the inner portion of bones, referred to herein as the marrow space, and contains the precursor stem cells that ultimately become red blood cells, white blood cells, and platelets.

Bone marrow aspirations and biopsies are common tests used to evaluate the bone marrow for leukemias and other hematologic disorders, for example. A sampling of the marrow from the marrow space can determine cell number, cell shape, and cell maturation. Special pathologic stains and molecular studies on the marrow specimens can establish certain diagnoses. Sampling of marrow from the marrow space may occur at multiple times during a patient's treatment program to assess progress.

Conventionally, in order to access bone marrow of a patient, the bone must be punctured each time a doctor needs to access the marrow. This is painful for the patient, and imposes a significant burden on the doctor and healthcare resources. There exists a need for an implantable bone marrow access apparatus that can be retained subcutaneously in the bone of a patient throughout the course of treatment to allow repeated access to the bone marrow without requiring repeated bone punctures.

SUMMARY OF THE INVENTION

An object of one or more embodiments of the present invention is to provide a bone marrow access system including a bone marrow access apparatus that allows repeated sampling of bone marrow at multiple timepoints without the need for repeated bone punctures through the bone cortex (the outer portion of the bone that has nerves which make punctures painful), tools for its installation and removal, and instruments with which it is used. The subcutaneous location of the apparatus, compared to an externalized device, is also likely to reduce infection from repeated sampling.

A bone marrow access system in accordance with the invention includes a bone marrow access apparatus adapted to be installed in connection with a bone. The bone marrow access apparatus includes a bone penetrating member having a seat and an internal channel having an opening at a proximal end and an opening at a distal end, and a valve cap around at least part of the bone penetrating member. The valve cap includes a valve having an opening having an open state in which the channel is not obstructed and a closed state preventing flow of material through the channel. The valve is typically repeatedly switchable between the open and closed states. The valve controls or regulates access to the channel by bone marrow sampling and biopsy instruments.

The system also includes a delivery tool for installing the bone marrow access apparatus in connection with the bone. The delivery tool includes a handle, an elongate, preferably rigid shaft attached at one end region to the handle, a flange attached to the shaft at an opposite end region of the shaft, and a drill bit extending outward from the shaft below the flange and attached to the flange and/or shaft. The flange is shaped to fit in the seat in the bone penetrating member and configured relative to the seat such that when the handle is rotated while the flange is in the seat, the bone penetrating member is rotated. As such, when the bone marrow access apparatus is installed by the delivery tool, the channel leads to the marrow space in the bone and is accessible to instruments through the valve and the channel.

The drill bit preferably has a length greater than a length of the channel below the seat such that when the flange is situated in the seat, the drill bit extends below a bottom surface the bone penetrating member. The seat and flange may have corresponding polygonal shapes.

The system may also include one or more instruments for accessing the marrow space while the bone marrow access apparatus is installed. Each instrument is dimensioned to pass through the valve and the openings of the channel to access the marrow space. Examples of instruments include straight sampling needles and curved sampling needles, the latter including a curved tip at a distal end that is capable of assuming a straight condition as it passes through the channel and may be provided with cutouts to improve its flexibility. The curvature of the tip allows for greater penetration into areas of the marrow space for sampling and biopsy purposes. The channel and instruments may have dimensions dependent on one another such that the instruments are tiltable while in the channel. For example, when the instrument has a size of 13 G, the channel may be provided with dimensions (e.g., width and height) to enable this instrument to tilt while in the channel by about 15 degrees all around. Similarly, when the instrument has a size of 15 G, the channel may be provided with dimensions to enable this instrument to tilt while in the channel by about 10 degrees all around.

In addition to or instead of the instruments, the system may include a removal tool for removing the bone marrow access apparatus from connection with the bone. The removal tool includes a handle, an elongate shaft attached at one end region to the handle, and a flange attached to the shaft at an opposite end region of the shaft. The flange is similarly shaped to fit in the seat, like the flange of the delivery tool, and configured relative to the seat such that when the handle of the removal tool is rotated while the flange of the removal tool is in the seat, the bone penetrating member is rotated. Thus, the flange of the removal tool, the flange of the delivery tool and the seat may all have the same shape.

BRIEF DESCRIPTION OF THE DRAWINGS

The present invention will be more fully understood from the following detailed description of embodiments thereof, taken together with the drawings, in which:

FIG. 9 is a perspective view of a delivery tool used for installing the bone marrow access apparatus shown in FIG. 1;

FIG. 10 is a view showing an initial installation stage of the bone marrow access apparatus shown in FIG. 1 with the delivery tool shown in FIG. 9;

FIG. 11 is a view showing the final installation stage of the bone marrow access apparatus shown in FIG. 1 with the delivery tool shown in FIG. 9;

FIG. 12 is a perspective view of a straight sampling needle used with the bone marrow access apparatus shown in FIG. 1;

FIG. 13 is a cross-sectional view of the sampling needle shown in FIG. 12 shown during use;

FIG. 14 is a perspective view of a sampling needle with a curved tip used with the bone marrow access apparatus shown in FIG. 1;

FIG. 16 is a perspective view of a removal tool used to remove the bone marrow access apparatus shown in FIG. 1 from its installation in a bone.

DETAILED DESCRIPTION OF THE INVENTION

Figure 1:
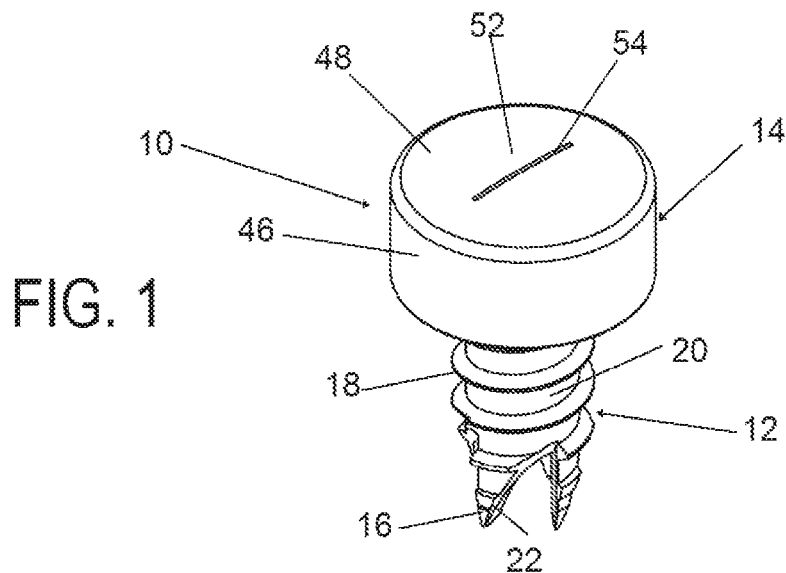
FIG. 1 is a perspective view of a bone marrow access apparatus in accordance with the invention.
Figure 2:
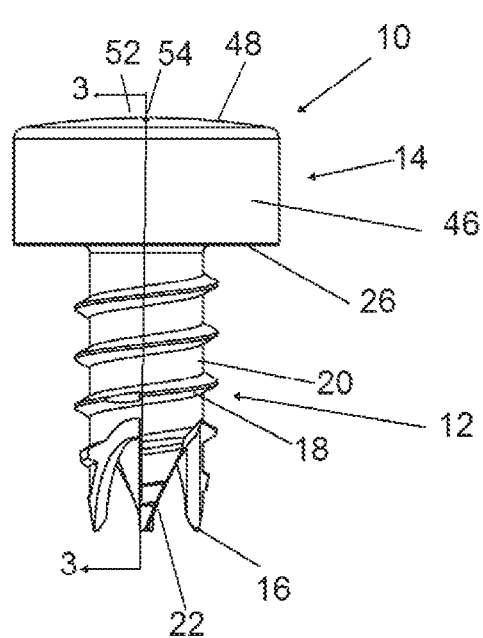
FIG. 2 is a front view of the bone marrow access apparatus shown in FIG. 1.
Figure 3:
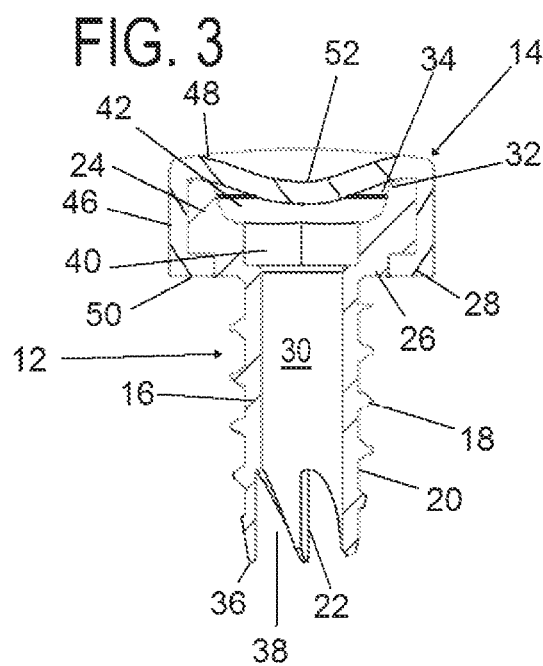
FIG. 3 is a cross-sectional view taken along the line 3-3 in FIG. 2.

Referring to the accompanying drawings wherein like reference numbers refer to the same or similar elements, FIGS. 1-3 show a bone marrow access apparatus 10 in accordance with the invention. Bone marrow access apparatus 10 includes a bone penetrating member 12 configured to penetrate into a bone across the bone cortex to enable access to a marrow space in the bone during use of the bone marrow access apparatus 10, and a valve cap 14 configured to control access to the marrow space through the bone penetrating member 12 and partly cover the bone penetrating member 12. The bone penetrating member 12 and valve cap 14 are formed as separate components and are engaged with one another in a secure manner for use of the bone marrow access apparatus 10.

Bone penetrating member 12 includes an axially extending, substantially tubular insertion portion 16 having a spiral thread 18 on an outer surface 20 (see FIG. 2). The spiral thread 18 enables the bone penetrating member 12 to be urged into the bone cortex upon rotation of the bone penetrating member 12 via a tool described below. An exterior surface of the insertion portion 16 can be provided with fluted edges 22 at the bottom thereof to help cut into the bone cortex during installation of the bone marrow access apparatus 10.

Spiral thread 18 aids in placement of the insertion portion 16 in the bone cortex, e.g., it enables the insertion portion 16 to be tapped or screwed into the bone cortex, and provides for secure retention of the insertion portion 16 in the bone cortex, and thus the bone marrow apparatus 10 in its use position in connection with the bone. Instead of a spiral thread 18, alternative structure may be provided on the outer surface 20 of the insertion portion 16 that functions to enable insertion of the bone penetrating member 12 into the bone cortex and retention therein. Such alternative structure is known to those skilled in the art to which this invention pertains, and all such structure that enables the insertion portion 16 to engage with and be retained in a bone is referred to as insertion and retention means herein. Details about the manner in which bone marrow access apparatus 10 is installed and used are described below.

Bone penetrating member 12 also includes a head portion 24 having a larger cross-sectional shape than that of the insertion portion 16. The head portion 24 has a bottom surface 26 adjacent the insertion portion 16 and a step 28 peripherally outward of the bottom surface 26. The step 28 provides an outer peripheral surface of the head portion 24 with a peripheral indentation which engages with part of the valve cap 14 to provide for secure engagement of the valve cap 14 to the bone penetrating member 12 as discussed below. The head portion 24 may have a hexagonal cross-section or a circular cross-section in a plane perpendicular to the axial direction of the bone penetrating member 12, or may have other cross-sectional shapes such as square, triangle, Torx, and the like.

An internal channel 30 extends through the bone penetrating member 12 between an opening 32 at a proximal end 34 in the upper surface of the head portion 24, and an opening 36 at a distal end 38 at the bottom of the insertion portion 16. Through channel 30, bone marrow can be removed from the marrow space in the bone when the bone marrow access apparatus 10 is engaged with the bone. Removal of bone marrow from the marrow space is commonly referred to as bone marrow sampling.

To this end, the axial length of the insertion portion 16 of the bone penetrating member 12 is dimensioned to at least reach the marrow space of a particular bone when the head portion 24 is on the surface of the bone (see FIG. 11). Thus, there may be a plurality of different lengths of insertion portions 16 of bone penetrating members 12, and a suitable length is selected based on the bone on which the bone penetrating member 12 is being installed and possibly also the size of the patient.

Part of the internal channel 30 is formed as a seat 40 below the upper surface of the head portion 24 (see FIG. 3). Seat 40 is designed to cooperate with various tools to enable the bone penetrating member 12 to be screwed into the bone and to facilitate removal of the bone marrow access apparatus 10 therefrom (discussed below). Seat 40 may have a particular shape or construction to enable rotation of the tools to impart rotation of the bone penetrating member 12 when the tools are mated with the seat 40 of the bone penetrating member 12. For example, a polygonal, e.g., hexagonal shape, for the seat 40 with a corresponding hexagonal shape for a flange of the tools is possible.

Another part of the channel 30 is formed as a valve relief space 42 (see FIG. 3). Valve relief space 42 is designed to accommodate leaflets of a valve 52 that are pushed inward into the channel 30 during installation and use of the bone marrow access apparatus 10 (see FIGS. 8-10).

Internal channel 30 has a particular size to enable bone marrow sampling when the bone marrow access apparatus 10 is in use. The channel 30 may have a diameter in a range from about 2.0 mm to about 4.2 mm (8-15 G) to allow for insertion of large-sized needles and other types of standardly used sampling instruments. The dimensions of the channel 30, i.e., its length and diameter, are also selected to enable tilting of a sampling needle to allow it to reach fresh areas of the marrow space after repeated sampling. The degree of tilting of the needle is thus dependent on the diameter of the needle and the diameter of the channel 30. In one embodiment, the channel 30 is dimensioned to enable a needle having a size of 13 G to tilt while in the channel by about 15 degrees in all directions relative to a central axis of the channel 30, thereby providing a total degree of tilt of about 30 degrees. In another embodiment, the channel 30 is dimensioned to enable a needle having a size of 15 G to tilt by about 10 degrees to each side, thereby providing a total degree of tilt of about 20 degrees. The 15 G needle may be used to sample cells via needle aspiration, while the 13 G instrument retrieves worm-like tissue samples and benefits more from tilting to source a fresh sampling area. Of course, different combinations of differently sized needles and channels 30 provide different tilt angles. A medical practitioner using bone marrow access apparatus 10 may be apprised of the needle sizes that can be used with each size of bone marrow access apparatus 10 and the obtainable tilt angles.

In a preferred embodiment, the bone penetrating member 12 is made of a rigid biocompatible material. Suitable materials include, without limitation, stainless steel, titanium, nitinol, and polyetheretherketone (PEEK).

Various constructions of the bone penetrating member 12 and valve cap 14 are envisioned to provide for secure retention of the valve cap 14 in connection with the bone penetrating member 12 for installation and use of the bone marrow access apparatus 10. One such construction is to provide the valve cap 14 with one or more walls that define an interior cavity 44 dimensioned to accommodate at least part of the bone penetrating member 12.

Figure 4:
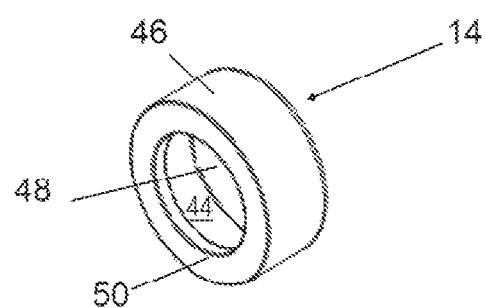
FIG. 4 is a rear perspective view of the valve cap of the bone marrow access apparatus shown in FIG. 1.

In the illustrated embodiment, the valve cap 14 includes a peripheral wall 46 arranged outward of the head portion 24 of the bone penetrating member 12 (see FIGS. 4 and 6) The peripheral wall 46 may entirely surround the head portion 24 of the bone penetrating member 12 with which the valve cap 14 is operatively engaged. The peripheral wall 46 has an inner surface having generally the same cross-sectional shape (in a plane perpendicular to the axis of the bone marrow access apparatus 10) as the outer surface of the head portion 24 of the bone penetrating member 12, and which is only slightly larger to provide for a tight fit between the valve cap 14 and the bone penetrating member 12.

Figure 6:
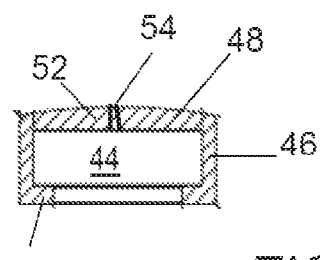
FIG. 6 is a cross-sectional view taken along the line 6-6 in FIG. 5.
Figure 5:
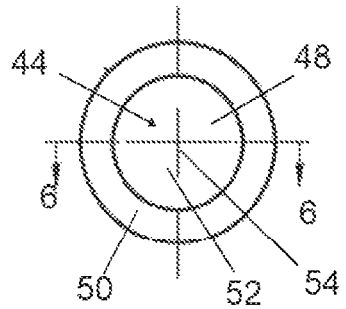
FIG. 5 is a rear view of the valve cap shown in FIG. 4.

Valve cap 14 also includes an upper wall 48 extending inward from an upper edge region of the peripheral wall 46 and a lower rim 50 extending inward from a lower edge region of the peripheral wall 46 (see FIG. 6). When the valve cap 14 is engaged with the bone penetrating member 12, the upper wall 48 is situated above the upper surface of the head portion 24 of the bone penetrating member 12 and the lower rim 50 is in the step 28 and thus underlies a peripheral edge region of the head portion 24 of the bone penetrating member 12 (see FIG. 3). With the upper wall 48 above the head portion 24 and the lower rim 50 in the step 28 below the head portion 24, the valve cap 14 is secured to the bone penetrating member 12.

Instead of upper wall 48 and lower rim 50, another structure for securing the valve cap 14 to the bone penetrating member 12, whether the head portion 24 or another part of the bone penetrating member 12, may be used in the invention. Such alternative securing structure which performs the same function as the upper wall 48 and lower rim 50 in the same or a similar manner is readily ascertainable by those skilled in the art to which this invention pertains and is considered to be within the scope of the invention. All such structure is considered to be encompassed within the phrase securing means for securing the valve cap to the bone penetrating member.

An important characteristic of the valve cap 14 is that at least the portion above the head portion 24 of the bone penetrating member 12 is made of atraumatic material, i.e., part or all of the upper wall 48. Soft elastomers known to be atraumatic may preferably be used. Use of atraumatic material prevents damage to the skin above the bone marrow access apparatus 10 when present in a human body. It is possible to form the valve cap 14 entirely from atraumatic material. Exemplifying characteristics of an atraumatic material include it being soft and having low durometer, with the purpose being to prevent skin erosion and degradation, and provide a cushion layer between the skin and the bone penetrating member.

The upper wall 48 includes a valve 52 situated entirely above the bone penetrating member 12 and that has an opening 54 that controls access to the channel 30 (see FIGS. 1 and 6). It is envisioned that the valve 52 may be situated in a part of the valve cap 14 other than in the upper wall 48. For example, the valve 52 may be invaginated (or recessed) into the channel 30 of the bone penetrating member 12.

Valve opening 54 has an open state in which the channel 30 is not obstructed and a default closed state in which it is closed and material flow between the openings 32, 36 of the channel 30 is prevented. In one embodiment, the valve cap 14 includes only a single valve.

Valve 52 has a particular construction to enable the valve opening 54 to be repeatedly switchable between the open and closed states. For example, the valve 52 may be a single slit valve as shown in FIG. 1, or alternatively, an intersecting slit valve. Such valves have leaflets 56 that contact one another in a default closed state and must be urged apart from one another to form the opening 54. When urged apart from one another, for example, by a sampling needle being introduced through the channel 30 into the marrow space in the bone, the leaflets 56 are accommodated in the valve relief space 42. Valve 52 may also be a duck-bill valve. Generally, the valve 52 is designed for repeated opening and closing of the opening 54, without losing integrity or releasing fragments thereof.

Valve 52 is representative of an access control component that controls access to the channel 30 and other access control components that perform the same functions for the valve 52 described herein may be used as alternative to the valve 52. Such alternative access control structure that performs the same function as the valve 52 in the same or a similar manner is readily ascertainable by those skilled in the art to which this invention pertains and is considered to be within the scope of the invention. A valve and all such comparable access control components are considered to constitute access control means for controlling access to the channel 30.

In one embodiment, the valve cap 14 has a unitary construction. This means that it is formed as a single unit or single piece. It can be entirely made of substantially the same soft elastomer, preferably one that has a durometer of 5-50 Shore A. For example, the valve cap 14 may be made of silicone or polyurethane.

Figure 7:
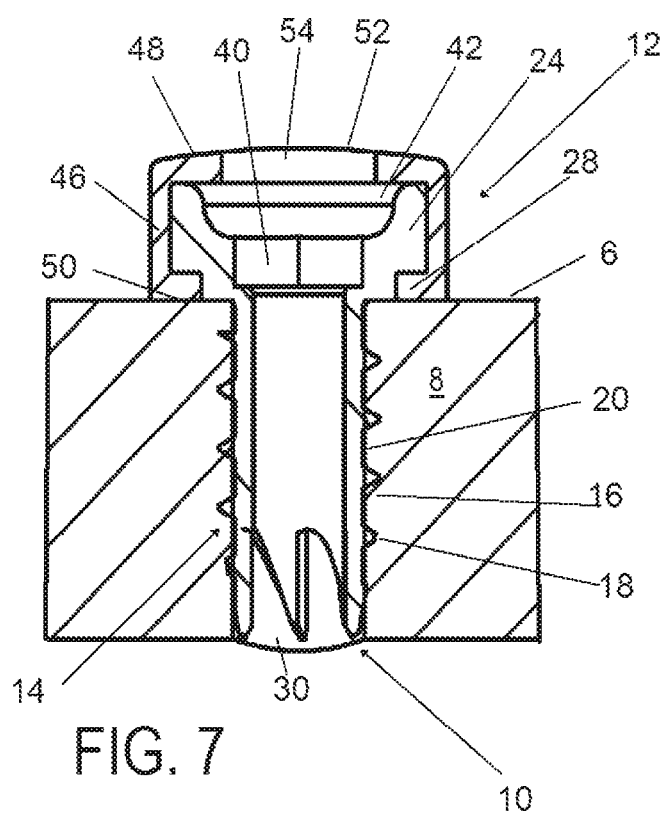
FIG. 7 is a cross-sectional view showing the bone marrow access apparatus installed in connection with a bone.

Bone marrow access apparatus 10 is installed in connection with a bone 8 since only part of the bone marrow access apparatus 10 is situated in the bone 8 (for example, the insertion portion 16 of the bone penetrating member 12 as shown in FIG. 7) while another part is situated on, above and/or outside of the bone 8 (for example, the head portion 24 of the bone penetrating member 12 and the valve cap 14 as shown in FIG. 7).

A typical, but non-limiting, installation of the bone marrow access apparatus 10 in connection with a bone entails first connecting the bone penetrating member 12 and the valve cap 14. This is achieved by inserting the head portion 24 of the bone penetrating member 12 through an opening defined by the lower rim 50 into the interior cavity 44 until the lower rim 50 has been urged into the step 28 in the head portion 24 of the bone penetrating member 12. The head portion 24 should fit snugly into the interior cavity 44 defined by the valve cap 14.

Figure 8:
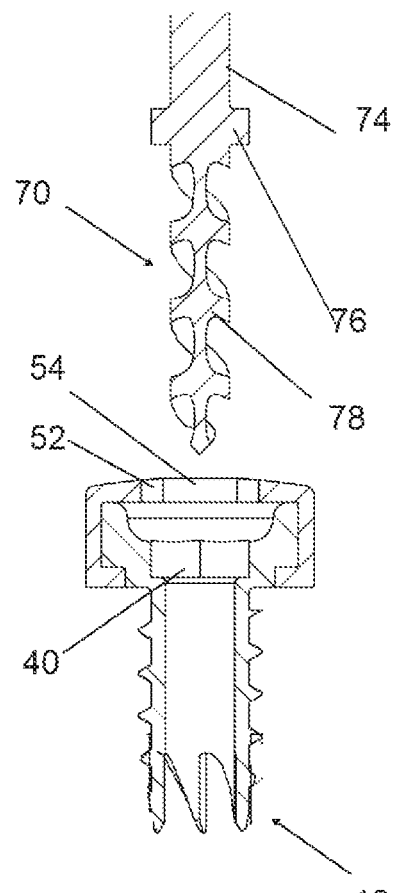
FIG. 8 is a view showing a preparatory stage for installation of the bone marrow access apparatus shown in FIG. 1.

For insertion of the insertion portion 16 of the bone penetrating member 12 into the bone 8, a delivery tool 70 is specially designed for this purpose, shown in FIGS. 8 and 9. Delivery tool 70 includes a handle 72, and a rigid, elongate shaft 74 attached at one end region to the handle 72 and attached at an opposite end region to a flange 76. A drill bit 78 is attached to the shaft 74 below the flange 76, or may be attached to the flange 76. Flange 76 is shaped to fit in the seat 40 in the head portion 24 of the bone penetrating member 12 (see FIGS. 10 and 11).

Dimensions of the delivery tool 70 are specific to the particular bone penetrating member 12 being installed, so that a plurality of delivery tools 70 may be required for differently dimensioned bone penetrating members 12. More particularly, the length of the drill bit 78 should be greater than the length of the channel 30 in the insertion portion 16 so that, when the flange 76 is situated in the seat 40, the drill bit 78 will extend below a bottom surface of the insertion portion 16 of the bone penetrating member 12 (see FIG. 11). This is necessary because the drill bit 78 often creates or completes drilling of a bone channel through the bone cortex to the marrow space 2, which bone channel starts with a pilot hole 4. Obviously, the diameter of the drill bit 78 must be smaller than the diameter of the channel 30 to enable the drill bit 78 to enter into and pass through the channel 30 (see FIGS. 10 and 11).

In an exemplifying installation method using the tool 70, the handle 72 of the delivery tool 70 is grasped and the drill bit 78 is aligned with the opening in the valve 52 leading to the channel 30 while the bone marrow access apparatus 10 has not yet been inserted into the bone 8 (FIG. 8). The drill bit 78 is then inserted through the opening 54 in the valve 52 into the channel 30 until the flange 76 rests on the seat 40 (FIG. 10).

The tool 70, with the attached bone marrow access apparatus 10, is inserted through an incision in the patient's skin to insert the insertion portion 26 of the bone penetrating member 12 into the pilot hole 4. The bone marrow access apparatus 10 is thus inserted into the pilot hole 4 in the bone 8 extending from the outer surface 6 of the bone 8 toward the marrow space 2, which pilot hole 4 may be only initially formed by the drill bit 78 (see FIG. 10). This insertion is aided by the thread 18 on the outer surface 20 of the insertion portion 16 of the bone penetrating member 12 which grips the surface of the bone cortex defining the pilot hole 4. In one embodiment, the pilot hole 4 may be formed by puncturing the bone 8 using a bone puncture needle. For example, the pilot hole 4 may be created through the cortical layer. Alternatively, the self-tapping delivery tool 70 can create the pilot hole 4 as it delivers the bone marrow access apparatus 10.

The tool 70 is then rotated, while maintaining the flange 76 in the seat 40, to cause the bone penetrating member 12 to be further inserted into the bone 8. Rotation of the tool 70 continues until the drill bit 78 completes a channel through the bone cortex into the marrow space 2 and the lower surface of the lower rim 50 of the valve cap 14 rests on the surface 6 of the bone 8 (FIG. 11).

By interposing the lower rim 50 between the head portion 24 of the bone penetrating member 12 and the surface 6 of the bone 8, a cushioning effect is provided by the lower rim 50. The lower rim 50 is preferably made of a soft elastomer which can be compressed and thereby cushions impact of the head portion 24 of the bone penetrating member 12 against the bone surface 6.

After the bone marrow access apparatus 10 attains the position shown in FIG. 11, the tool 70 is removed from engagement with the bone marrow access apparatus 10 by lifting it upward. The tool 70 is then removed through the opening 54 defined by the valve 52 causing the opening 54 in the valve 52 to close. The tissues above the apparatus are then surgically closed. The final installed position of the bone marrow access apparatus 10 is shown in FIG. 7. Note that glue or another adhesive is not required to install the bone marrow access apparatus 10.

Once the bone marrow access apparatus 10 is installed in connection with a bone 8, it can be used for sampling bone marrow whenever such sampling is desired either for biopsy or aspiration dependent on which instrument is used. Each time bone marrow is sampled, the surgeon would press the skin in the known area of the bone marrow access apparatus 10 to locate the bone marrow access apparatus 10. Once located, the surgeon would press the skin over the valve cap 14, and insert an instrument such as a sampling needle through the skin and through the opening 54 of the valve 52 into the channel 30 and out of the distal opening 36 of the channel 30 into the marrow space 2. A sampling needle, or other type of instrument, having a size (gauge) that fits in the channel 30 is obviously selected. The penetration depth of the sampling needle or other instrument into the marrow space 2 is also variable by the surgeon.

If a straight sampling needle 66 is selected, the sampling needle 66 may be tilted to sample a fresh area of the marrow space 2 for bone marrow (see FIGS. 12 and 13).

Figure 15:
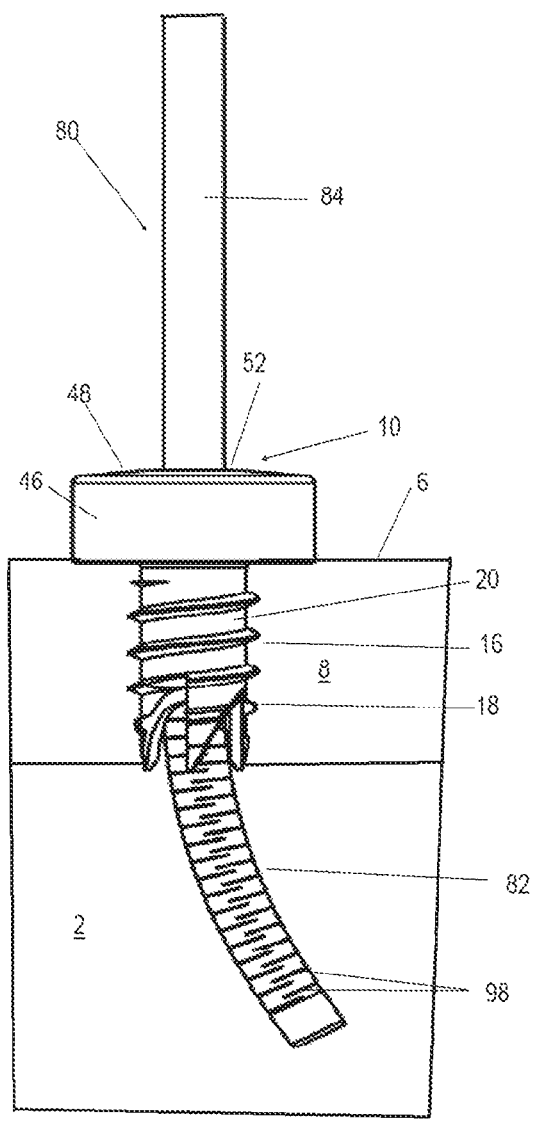
FIG. 15 is a cross-sectional view of the sampling needle with a curved tip shown in FIG. 14 shown during use.

As an alternative, a curved sampling needle 80 may be used (FIG. 14). The curved sampling needle 80 includes an inner tube 82 with a curve at a distal end and a straight outer tube 84. The curved inner tube 82 allows for sampling bone marrow from a larger region of the marrow space 2 since it can be inserted to different depths and rotated to reach different directions (see FIG. 15). To aid in curving of the inner tube 82, it is optionally provided with cut-outs 98 at the distal end region. These cutouts 98 may be formed by a laser.

Curved sampling needle 80 may be made of nitinol and the curved inner tube 82 sharpened to facilitate for penetration of the marrow. The curved inner tube 82 assumes a straight condition as it passes through the channel 30 since it is retained in the straight outer tube 84, but then curves to its initial condition after passing through the opening 36 and then out of the outer tube 84 (FIG. 14). The inner tube 82 is made of a material that is sufficiently rigid to push through the outer tube 84 in order to collect a tissue sample, yet configured to revert to a curved state at the distal end to increase the sampling area, and such materials are readily known or ascertainable to those skilled in the art to which this invention pertains in view of the disclosure herein. Instead of a straight outer tube 84, a straight internal stylet may be provided to allow for entry of the curved inner tube 82 into and passage through the channel 30, and then unsheathing of the inner tube 82 to enable it to return to its natural curve when reaching the marrow space for sampling.

In one embodiment, the needles 66, 80 have a stylet that allows the needles 66, 80 to penetrate the skin and get to the location in the marrow space of the bone. The stylet is removed allowing the hollow channel to now be able to aspirate the marrow or biopsy it. Without using the stylet, the needles 66, 80 would core the skin and muscles as they are pushed in. It is also possible to use a guide needle that would, with a stylet, be pushed into the marrow space and then when the stylet is removed, different needles could be inserted through the channel to sample marrow without having to penetrate the skin fresh with each needle.

Regardless of which type of sampling needle is used, after the sampling is completed, the needle is removed from the channel 30 and withdrawn through the valve 52 and skin. The valve 52 closes its opening 54 thereby preventing material flow out of and into the marrow space 2.

The sampling needles 66, 80 preferably include depth of insertion indicators so that the surgeon can read the indicators and determine the sampling depth. This allows the surgeon to sample different depths in the bone marrow space 2 at different times, for example, to sample at week 1 at X depth and week 2 at a different Y depth.

Once the bone marrow access apparatus 10 is no longer needed for bone marrow sampling, it can be removed. Removal generally involves rotating the bone marrow access apparatus 10 out of the hole in the bone 8. If provided with a spiral thread 18, this may be attained by grasping the valve cap 14, applying pressure against the head portion 24 of the bone penetrating member 12 and then rotating it in the opposite direction than the direction in which bone penetrating member 12 was inserted into the hole in the bone 8.

A removal tool 86 is specially designed to ease removal of the bone marrow access apparatus 10 (FIG. 16). Removal tool 86 includes a handle 88, and a shaft 90 attached at one end region to the handle 88 and attached at an opposite end region to a flange 92. Flange 92 is shaped to fit in the seat 40 in the head portion 24 of the bone penetrating member 12.

Figure 17:
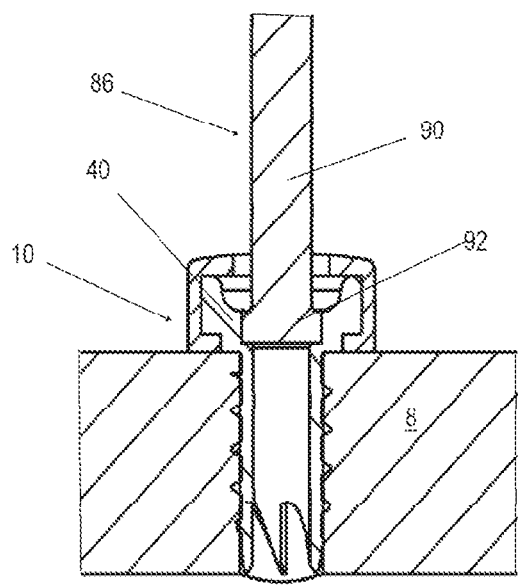
FIG. 17 is a view showing the manner in which the bone marrow access apparatus shown in FIG. 1 can be removed using a removal tool.

For removal of the bone marrow access apparatus 10, the surgeon inserts the removal tool 86 through an opening in the skin over the bone marrow access apparatus 10 and then inserts the removal tool 86 through the opening 54 in the valve 52 into the channel 30 until the flange 92 rests on the seat 40 (FIG. 17). The tool 86 is then rotated, while maintaining the flange 92 in the seat 40, to cause the bone penetrating member 12 to withdraw from the bone hole. Rotation of the tool 86 continues until the insertion portion 16 of the bone penetrating member 12 is completely free of the bone and then the tool 86 and bone marrow access apparatus 10 engaged therewith is withdrawn through the skin of the patient. The valve cap 14 holds the bone penetrating member 12 on the removal tool 86 as it is lifted up. The leaflets 56 will be on the top of the flange of the removal tool 86 with some counterforce.

Delivery and removal tools 70, 86 may be single use tools or designed for multiple uses.

Variations of the embodiments described above and illustrated in the drawings are considered to be within the scope of the invention, and thus the scope of the invention should be determined by the appended claims and their legal equivalents, rather than by the examples given. In addition, apparatus and methods disclosed in U.S. provisional patent application Ser. No. 62/062,105 filed Oct. 9, 2014, U.S. provisional patent application Ser. No. 62/404,551 filed Oct. 5, 2016 and U.S. nonprovisional patent application Ser. No. 15/024,522 filed Mar. 24, 2016 may be incorporated into and/or used with the inventions disclosed above and all of these applications are incorporated by reference herein.

The invention claimed is:

1. A bone marrow access apparatus, comprising:
a bone penetrating member having an internal channel having an opening at a proximal end and an opening at a distal end; and
a cap engaged with the bone penetrating member, the cap defining an interior cavity in which part of the bone penetrating member is situated,
wherein:
the bone penetrating member comprises an axially extending insertion portion and a head portion having a larger cross-sectional area than the insertion portion,
the head portion has a distally-facing bottom surface adjacent the insertion portion and a step peripherally outward of the bottom surface and providing an outer peripheral surface of the head portion with an indentation, the step being adjacent to the bottom surface, recessed proximally with respect to the bottom surface, and having a surface that faces distally,
the cap comprises a peripheral wall, an upper wall coupled to an upper edge region of the peripheral wall, and a lower rim coupled to a lower edge region of the peripheral wall, the interior cavity being defined by the upper wall, the peripheral wall, and the lower rim, and
the lower rim extends inward from the peripheral wall into the indentation to thereby secure the cap to the bone penetrating member.

2. A bone marrow access apparatus subcutaneously implantable in a bone of a patient to enable biopsy of bone marrow, the bone marrow access apparatus comprising:
a bone penetrating member having threads on an outer surface thereof and an internal channel having an opening at a proximal end and an opening at a distal end, the threads having a hardness and sharpness such that the bone penetrating member is screwable into the bone to access the bone marrow; and
a valve cap engaged with the bone penetrating member, the valve cap defining an interior cavity in which part of the bone penetrating member is situated,
wherein:
the valve cap comprises a valve having an opening having an open state in which the channel permits flow of material therethrough and a closed state preventing flow of material through the channel,
the valve is repeatedly switchable between the open and closed states,
the channel is sized to receive an instrument for obtaining a biopsy of the bone marrow, and
the valve cap comprises a peripheral wall having an upper edge region to which an upper wall including the valve is coupled such that the valve is situated above an upper surface of the bone penetrating member, and a lower edge region to which a lower rim is coupled, the lower rim extending inward from the peripheral wall to underlie part of the bone penetrating member so as to be positioned between the part of the bone penetrating member and the bone when the bone marrow access apparatus is implanted in the bone of the patient, thereby providing a cushion between the bone and the part of the bone penetrating member, and so as to secure the valve cap to the bone penetrating member, the peripheral wall being situated outward of the part of the bone penetrating member.

3. The apparatus of claim 2, wherein at least a portion of the valve cap above an upper surface of the head portion of the bone penetrating member is made of an elastomer.

4. The apparatus of claim 2, wherein the entire valve cap, including the peripheral wall, the upper wall, and the lower rim, is a one-piece member made of an elastomer.

5. The apparatus of claim 2, wherein the opening of the valve is a slit in the upper wall which is present in the upper wall regardless of the presence or absence of any instrument is inserted through the valve.

* * * * *